United States Patent [19]
Patel et al.

[11] Patent Number: 5,747,436
[45] Date of Patent: May 5, 1998

[54] LOW STATIC CONDITIONING SHAMPOO

[75] Inventors: Amrit M. Patel; Suman K. Chopra, both of Dayton, N.J.

[73] Assignee: Colgate-Palmolive Company, New York, N.Y.

[21] Appl. No.: 783,159

[22] Filed: Jan. 14, 1997

Related U.S. Application Data

[60] Provisional application No. 60/009,398, Jan. 16, 1996.

[51] Int. Cl.$^6$ ..................................... A61K 7/075
[52] U.S. Cl. ..................... 510/124; 510/122; 510/125; 510/126
[58] Field of Search .................... 510/122, 125, 510/126, 124, 123; 424/70.12, 70.19, 70.28, 70.122, 70.13

[56] References Cited

U.S. PATENT DOCUMENTS

| | | | |
|---|---|---|---|
| 3,904,359 | 9/1975 | Ramachandran | 8/137 |
| 3,950,417 | 4/1976 | Verdicchio et al. | 252/545 |
| 4,246,131 | 1/1981 | Lohr | 252/153 |
| 4,275,055 | 6/1981 | Nachtigal et al. | 424/70 |
| 4,368,127 | 1/1983 | Richmond | 252/8.8 |
| 4,559,151 | 12/1985 | Pregozen et al. | 252/8.8 |
| 4,559,227 | 12/1985 | Chandra et al. | 424/70 |
| 4,631,187 | 12/1986 | Padden et al. | 424/70 |
| 4,741,855 | 5/1988 | Grote et al. | 252/142 |
| 4,804,497 | 2/1989 | Urfer et al. | 252/8.8 |
| 4,842,760 | 6/1989 | Tsumadori et al. | 252/8.8 |
| 4,895,667 | 1/1990 | Fox et al. | 252/8.8 |
| 4,895,722 | 1/1990 | Abe et al. | 424/71 |
| 4,910,013 | 3/1990 | Kanamaru et al. | 424/47 |
| 4,954,335 | 9/1990 | Janchipraponvej | 424/70 |
| 4,997,641 | 3/1991 | Hartnett et al. | 424/70 |
| 5,078,990 | 1/1992 | Martin et al. | 424/70 |
| 5,106,613 | 4/1992 | Harnett et al. | 424/71 |
| 5,152,914 | 10/1992 | Forster et al. | 252/174 |
| 5,213,716 | 5/1993 | Patel et al. | 252/547 |
| 5,236,615 | 8/1993 | Trish et al. | 252/174 |
| 5,248,445 | 9/1993 | Rizvi | 252/174.15 |
| 5,259,964 | 11/1993 | Chavez et al. | 252/8.6 |
| 5,277,899 | 1/1994 | McCall | 424/71 |
| 5,346,642 | 9/1994 | Patel et al. | 252/174.21 |
| 5,348,736 | 9/1994 | Patel et al. | 424/70 |

FOREIGN PATENT DOCUMENTS

| | | |
|---|---|---|
| 0 255 604 A1 | 2/1988 | European Pat. Off. |
| 0 598 531 A2 | 5/1994 | European Pat. Off. |
| 44 04 493 C1 | 1/1995 | Germany. |
| 57-53600 | 3/1982 | Japan. |
| 63-8493 | 1/1988 | Japan. |

OTHER PUBLICATIONS

Trade Literature–Dow Corning® Q2–5220 Surfactant, 1992.
Trade Literature–Dow Corning® Q2–5324 Fluid, 1992.
Trade Literature–Dow Corning® Q2–5220 Resin Modifier, 1986.

*Primary Examiner*—Ardith Hertzog
*Assistant Examiner*—Gregory Webb
*Attorney, Agent, or Firm*—Richard J. Ancel; Rosemary M. Miano

[57] ABSTRACT

The present invention provides an effective conditioning shampoo composition which is free of conditioning amounts of silicone conditioning agents. It comprises: A) about 5% to about 40% of a detersive surfactant mixture of an anionic detergent and an amphoteric surfactant, the weight ratio of the anionic detergent to the amphoteric surfactant being in the range of about 10:1 to 0.8:1; B) about 0.05% to about 6% of a conditioning agent selected from the group consisting of 0.05% to 5% of a complex of essentially equimolar amounts of a $C_8$–$C_{18}$(EtO)$_{1-10}$ carboxylic acid, and a $C_8$–$C_{18}$ alkyl (EtO)$_{0-10}$ dimethyl amine; 0.05% to 1.0% of a polyquaternary compound selected from the group consisting of a quaternized cellulosic polymer and a mixture of the quaternized cellulosic polymer with a non-cellulosic quaternary conditioning polymer; and mixtures of the foregoing; C) 0.1% to 1% of a static control mixture of a quaternary ammonium salt having the formula $R_9, R_{10}, R_{11}, R_{12}N^+X^-$ wherein $R_9$ is a $C_{14}$–$C_{18}$ alkyl, $R_{10}$ and $R_{11}$ are each a $C_1$–$C_4$ alkyl, $R_{12}$ is $C_1$–$C_4$ alkyl or benzyl and $X^-$ is a salt forming cation selected from the group consisting of chloride, bromide, methosulfate and ethosulfate; and a di-quaternary ammonium salt having the formula $(R_{13})_2R_{14}R_{15}N^+X^-$ wherein $R_{13}$ is a $C_{14}$–$C_{18}$ alkyl or alkylene group and $R_{14}$ and $R_{15}$ are each a $C_1$–$C_4$ alkyl group or a $(CH_2CH_2O)_nH$ group with at least one of $R_{14}$ and $R_{15}$ being a $(CH_2CH_2O)_n$ H group, n is an integer from 2 to 20 and X is a cation as set forth above, the weight ratio of the monoalkyl quaternary salt to dialkyl quaternary salt being from about 1:4 to 4:1; and D) an aqueous medium. These compositions exhibit enhanced antistatic properties as compared to the same compositions containing either the monoalkyl quaternary salt or the dialkyl quaternary salt as the sole antistatic ingredient.

14 Claims, No Drawings

LOW STATIC CONDITIONING SHAMPOO

This application claims the benefit of U.S. Provisional application Ser. No. 60/009,398 filed Jan. 16, 1996.

The instant invention is generally directed to a novel, effective, conditioning shampoo which is free of conditioning amounts of silicone conditioning agents and exhibits enhanced antistatic properties due to the use of a mixture of a $C_{14}$–$C_{18}$ alkyl quaternary ammonium salt and a di-$C_{14}$–$C_{18}$ alkyl ethoxylated quaternary salt as the antistatic agent. The improved shampoos contain a mixture of a sulfated or sulfonated anionic detergent having a higher alkyl group and an amphoteric detergent as the foaming and cleansing surfactant and a conditioning agent which may be a cellulosic polyquat or a complex of a $C_8$–$C_{18}$ carboxylic acid and a $C_8$–$C_{18}$ alkyl dimethyl amine or a mixture thereof. Such shampoos may be prepared either in clear or opaque form and are ultra-mild when balanced proportions of anionic and amphoteric/cationic materials are employed. Antidandruff agents may be included, too.

BACKGROUND OF THE INVENTION

While the conditioning shampoos have achieved a great deal of success in the marketplace, such products suffer, at least among a certain segment of consumers, negative attributes of poor appearance, decreased foam, reduced viscosity, and physical instability because of the conditioning materials therein. For example, when high-molecular weight silicone derivatives are added to achieve the conditioning benefits, it has been found that it is difficult to formulate silicone-containing shampoos that are stable and do not suffer from the separating out of the silicone ingredient. The most accepted way to incorporate these silicone conditioning agents in such conditioning shampoos is to disperse, suspend, or emulsify them, which results in the opacification of these products and sometimes results in unstable products due to the separation of the emulsified or suspended silicone.

The patent literature relating to detergent compositions which include water-insoluble, hair and skin conditioning materials reflects a variety of approaches designed to overcome the above mentioned disadvantages. More specifically, the patent literature teaches a variety of agents that disperse, suspend, or emulsify silicone conditioning agents. For example, U.S. Pat. No. 4,741,855 to Grote et al teaches the use of long chain ($C_{16}$–$C_{22}$) acyl derivatives, such as ethylene glycol distearate or long chain ($C_{16}$–$C_{22}$) amine oxides, as suspending agents for water-insoluble silicone conditioning agents; and U.S. Pat. No. 5,152,914 to Forster et al teaches the use of suspending agents chosen from polyethylene glycol mono- or diesters of $C_{16}$–$C_{22}$ fatty acids having from 2 to 7 ethylene oxide groups for suspending said silicone conditioners. Also, U.S. Pat. No. 4,997,641; U.S. Pat. No. 5,106,613; U.S. Pat. No. 5,213,716; U.S. Pat. No. 5,346,642; and U.S. Pat. No. 5,348,736, all assigned to the assignee of the instant invention, disclose the use of long chain ($C_{24}$–$C_{45}$) alcohols and ethoxylated alcohols as suspending agents. Alternatively, U.S. Pat. No. 4,559,227 to Chandra et al discloses conditioning shampoos in the form of clear solutions wherein blends of amine-functional siloxane polymers and nonionic surfactants of the alkanolamide or amine oxide type are dissolved in aqueous solutions containing typical anionic and amphoteric detergents used in shampoos. However, the commercial availability of the latter compositions has not been assessed.

Because the water-insoluble conditioning agents affect the physical and performance characteristics of the resultant shampoos, it is difficult to reformulate the shampoos to overcome the aforementioned problems. In research on conditioning shampoos, it has been noted that the conditioning agent directly affects the viscosity, clarity and stability of the resultant liquid shampoo and also affects the cleansing, conditioning, foaming and anti-static properties at use concentrations of said shampoo. Some of these problems were encountered in attempts to formulate a satisfactory conditioning shampoo which does not contain conditioning proportions of water-insoluble silicone conditioning agents. For example, in attempts to formulate a conditioning shampoo without a water-insoluble silicone conditioning agent to achieve a lower cost shampoo without silicone stability problems, viscosity, cleansing, conditioning and antistatic properties were affected.

It has now been discovered that it is possible to formulate aqueous conditioning shampoo compositions which do not contain a water-insoluble silicone conditioning agent by using selected proportions of anionic and amphoteric detergents, selected conditioning agents and a particular antistatic mixture of cationic surfactants. Such compositions may be prepared in clear or opaque form and are high foaming with good conditioning effects at use concentrations. Furthermore, in one aspect involving controlled proportions of anionic and amphoteric/cationic components, ultra mild shampoos are achieved which do not cause irritation to the skin.

It is recognized that the prior art discloses compositions containing essentially equimolar quantities of anionic surfactant and amphoteric surfactant. For example, U.S. Pat. No. 3,950,417 of Verdicchio et al. discloses a shampoo containing nonionic surfactant, a surfactant betaine and an anionic surfactant wherein the molar ratio of betaine to anionic is from 0.9:1 to 1.1:1. However, the nonionic detergent is the principal surfactant in the preferred compositions which of necessity exhibit reduced foaming. Similarly, U.S. Pat. No. 4,246,131 of Lohr discloses a low irritant, clear composition containing an equimolar mixture of surfactant betaine and alkanolamine neutralized, anionic, alkyl sulfate detergent. However, the prior art compositions do not include conditioning agents or anionic hydrotropic sulfonates/sulfates and do not recognize the need for balanced molecular proportions of the anionic and amphoteric/cationic ingredients therein. Therefore, said compositions should not provide effective hair and skin conditioning benefits.

On the other hand, European Application EP 0 294 894 A2 discloses an ion pair complex of an anionic surfactant, an alkyl amine and a wax as a conditioning agent and discloses anionic surfactant based shampoos containing said complex as a conditioning agent. However, again there is no recognition of the need for balanced molar proportions of anionic and amphoteric/cationic ingredients in the final composition. Furthermore, the prior art does not disclose or suggest conditioning shampoos having enhanced antistatic properties due to the presence of an antistatic mixture of mono $C_{14}$–$C_{18}$ alkyl quaternary salt and di-$C_{14}$–$C_{18}$ alkyl ethoxylated quaternary salt.

SUMMARY OF THE INVENTION

As described above, the present invention resides in the discovery that effective, low cost conditioning shampoos can be prepared without conditioning proportions of the expensive silicone conditioning agents. The resultant shampoos have good foaming, cleansing and conditioning properties and exhibit improved antistatic properties in use because of the use of a mixture of specific mono-alkyl and dialkyl quaternary ammonium antistatic agents. Hair washed with such shampoos exhibits less static than is obtained when a similar shampoo containing either one of the antistatic agents is employed. Furthermore, compositions which are very mild to the skin are obtained when balanced molecular proportions of selected anionic surfactants and amphoteric/cationic materials are employed.

Broadly, the present invention relates to an effective conditioning shampoo composition which is free of conditioning amounts of silicone conditioning agents comprising by weight:

A. about 5% to about 40% of a detersive surfactant mixture of:
  (1) an anionic detergent selected from the group consisting of $C_8$–$C_{18}$ alkyl sulfates, $C_8$–$C_{18}$ alkyl ethenoxy ether sulfates containing 1 to 12 ethenoxy groups in the molecule, $C_8$–$C_{18}$ acyl isethionates, $C_{10}$–$C_{20}$ alkyl sulfonates, $C_{10}$–$C_{22}$ alkene sulfonates, and mixtures thereof; and
  (2) an amphoteric surfactant selected from the group consisting of $C_8$–$C_{18}$ alkyl betaines and sulfobetaines, $C_8$–$C_{18}$ alkyl amido, $C_2$–$C_3$ alkyl betaines and sulfobetaines, $C_8$–$C_{18}$ alkyl amphoacetates, $C_8$–$C_{18}$ alkyl amphopropionates, and mixtures thereof; the weight ratio of said anionic detergent to said amphoteric detergent being in the range of about 10:1 to 0.8:1;

B. about 0.05% to about 6% of a conditioning agent is selected from the group consisting of:
  (1) 0.05% to 5% of a complex of essentially equimolar amounts of a $C_8$–$C_{18}$ (EtO)$_{1-10}$ carboxylic acid, and a $C_8$–$C_{18}$ alkyl (EtO)$_{0-10}$ dimethyl amine;
  (2) 0.05% to 1.0% of a polyquaternary compound selected from the group consisting of a quaternized cellulosic polymer and a mixture of said quaternized cellulosic polymer with a non-cellulosic quaternary conditioning polymer; and
  (3) mixtures of the foregoing;

C. 0.1% to 1% of a static control mixture of:
  (1) a quaternary ammonium salt having the formula $R_9$, $R_{10}$, $R_{11}$, $R_{12}N^+X^-$ wherein $R_9$ is a $C_{14}$–$C_{18}$ alkyl, $R_{10}$ and $R_{11}$ are each a $C_1$–$C_4$ alkyl, $R_{12}$ is $C_1$–$C_4$ alkyl or benzyl and $X^-$ is a salt forming cation selected from the group consisting of chloride, bromide, methosulfate and ethosulfate; and
  (2) a di-quaternary ammonium salt having the formula $(R_{13})_2R_{14}R_{15}N^+X^-$ wherein $R_{13}$ is a $C_{14}$–$C_{18}$ alkyl or alkylene group and $R_{14}$ and $R_{15}$ are each a $C_1$–$C_4$ alkyl group or a $(CH_2CH_2O)_nH$ group with at least one of $R_{14}$ and $R_{15}$ being a $(CH_2CH_2O)_nH$ group, n is an integer from 2 to 20 and x is a cation as set forth in C(1) above; the weight ratio of the monoalkyl quaternary salt to dialkyl quaternary salt being from about 1:4 to 4:1; and D. the balance being an aqueous medium; said compositions exhibiting enhanced antistatic properties as compared to the same compositions containing either said monoalkyl quaternary salt or said dialkyl quaternary salt as the sole antistatic ingredient.

In use concentrations in water, the shampoos exhibit good foam and cleaning and deliver the conditioning agent in water-insoluble form.

In one preferred aspect, the described invention contains as the conditioning agent a mixture of (a) a quaternized cellulose polymer and (b) a complex of essentially equimolar amounts of $C_8$–$C_{18}$ (EtO)$_{1-10}$ carboxylic acid and $C_8$–$C_{18}$ alkyl (EtO)$_{0-10}$ dimethyl amine polyoxy ($C_2$–$C_3$) alkylene copolymer. The preferred compositions exhibit enhanced conditioning properties due to the use of the mixture of conditioning agents.

Furthermore, by utilizing the specified conditioning materials individually and in mixtures, a line of conditioning shampoos providing low, medium and high conditioning effects can be marketed by a manufacturer.

In a second preferred aspect the sum of the moles of anionic surfactants—anionic detergent and anionic hydrotropic sulfonate/sulfate—is substantially equal to the sum of the moles of amphoteric detergent and cationic materials at a pH in the range of 5.5 to 7.0 and the resultant conditioning shampoos are very mild to the skin at use concentrations in water.

In a further preferred aspect, the inventive shampoos include a non-conditioning proportion—0.05% to 0.30% by weight—of water-insoluble silicones which are soluble in the aqueous detergent as a plasticizer for the hair. In use, the non-conditioning proportion of silicone is effective to smooth the surface of the hair, with the most beneficial effects being achieved by use of a mixture of lauryl methicone copolyol and polydimethylsiloxane-polyether copolymers in a weight ratio of about 1:2 to 2:1.

DETAILED DESCRIPTION OF THE INVENTION

Anionic Detergents

The suitable anionic detergents are employed in the form of their water-soluble salts and the salt forming cation usually is selected from the group consisting of sodium, potassium, ammonium and mono-, di- and tri- $C_2$–$C_3$ alkanolammonium, with the sodium and ammonium cations being preferred.

The suitable anionic detergents include the following:

1. The $C_8$–$C_{18}$ alkyl ether ethenoxy sulfates of the formula

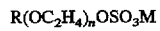

$$R(OC_2H_4)_nOSO_3M$$

wherein n is 1 to 12, preferably 1 to 5. These sulfates differ from the primary alkyl sulfate detergent in the number of moles of ethylene oxide (1–12) reacted with one mole of alkanol in forming the ethoxylated alkanol which is sulfated and neutralized to form this anionic detergent. The most preferred alkyl ether ethenoxy sulfates contain 12 to 16 carbon atoms in the alkyl group and contain two to three ethylene oxide groups per mole of alkanol.

2. The $C_8$–$C_{18}$ alkyl sulfates which are usually obtained by sulfating $C_8$–$C_{18}$ alkanols obtained by reducing the glycerides of tallow or coconut oil. Preferred alkyl sulfates contain 10 to 16 carbons in the alkyl group.

3. The O–$C_8$–$C_{18}$ acyl isethionates may be produced by neutralizing the reaction product of a $C_8$–$C_{18}$ alkanoic acid with 2-hydroxyethanesulfonic acid. Similar to the sarcosines and taurines, the preferred isethionates contain 12 to 14 carbon atoms in an acyl group obtained by reduction of coconut oil.

4. The $C_{10}$–$C_{20}$ paraffin sulfonates obtained, for example, by reacting an alpha-olefin with bisulfite. Preferred alkane sulfonates contain 13 to 17 carbon atoms in the alkyl group.

5. The $C_{10}$–$C_{22}$ olefin sulfonates which may be obtained by sulfating the appropriate olefin. Preferred olefin sulfonates contain from 14 to 16 carbon atoms in the alkyl group and are obtained by sulfonating an alpha-olefin.

While mixtures of the foregoing anionic detergents may be employed, the preferred anionic detergents are the sodium and ammonium salts of the alkyl ethenoxy ether sulfates and the alkyl sulfates.

Generally, the minimum proportion of the anionic detergent will be at least about 2% by weight of the shampoo.

Other Anionic Surfactant

In addition to the anionic detergent discussed above, the described inventive compositions may include anionic, hydrotropic $C_1$–$C_3$ alkyl substituted benzene sulfonates and $C_5$–$C_6$ alkyl sulfates. These materials are classified as surfactant-hydrotropes and serve to solubilize the anionic and amphoteric detergent in the aqueous medium. Also, it is believed that these materials assist in removing soil from the substrates being cleaned. Usually, these materials are used in the form of their water soluble sodium, potassium and ammonium salts. Suitable hydrotropic sulfonate and sulfate salts include the salts of toluene sulfonate, xylene sulphonate, cumene sulfonate, $C_5$–$C_6$ alkyl sulfate and mixtures thereof.

The proportion of the hydrotropic sulfonate or sulfate material generally will be in the range of about 0.5% to about 5% by weight of the resultant composition. Preferably the range of this material will be about 0.5% or 1% to 4% by weight of the final composition.

Amphoteric Surfactants

Generally, the amphoteric surfactant components will be selected from the group consisting of $C_8$–$C_{18}$ alkyl betaines and sulfobetaines, and $C_8$–$C_{18}$ alkyl amphoacetates and propionates. The suitable betaines and sulfobetaines have the following formula:

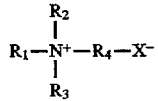

wherein $R_1$ is an alkyl group having 8 to about 18 carbon atoms, preferably 10 to 16 carbon atoms or the alkylamido radical:

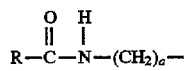

wherein RCO is an acyl group having 8 to about 18 carbon atoms and a is the integer 1 to 4: $R_2$ and $R_3$ are each alkyl groups having 1 to 3 carbon atoms and preferably 1 carbon; $R_4$ is an alkylene or hydroxyalkylene group having from 1 to 4 carbon atoms and optionally, one hydroxyl group; and X is an anion selected from the group consisting of $SO_3^=$ and $COO^=$. Typical betaines and amido alkyl betaines include decyl dimethyl betaine or 2-(N-decyl-N,N-dimethylammonio) acetate, cocodimethyl betaine or 2-(N-coco-N,N-dimethylammonio) acetate, myristyl dimethyl betaine, palmityl dimethyl betaine, lauryl dimethyl betaine, cetyl dimethyl betaine, stearyl dimethyl betaine, cocoamidopropyl dimethyl betaine and laurylamidoethyl dimethyl betaine. Typical sulfobetaines or sultaines similarly include cocodimethyl sulfobetaine, or 3-(N-coco-N,N-dimethylammonio) propane-1 sulfonate, myristyl dimethyl sulfobetaine, lauryl dimethyl sulfobetaine, cocoamidoethylsulfobetaine and cocamidopropylhydroxy sultaine.

Other suitable amphoteric detergents are the $C_8$–$C_{18}$ alkyl amphoacetates and propionates corresponding to the following formula:

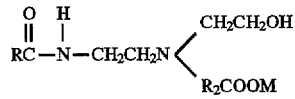

wherein RC(O) is a $C_8$–$C_{18}$ acyl group, $R_2$ is a $C_1$–$C_2$ alkyl group and M is a salt forming group such as sodium or potassium. A substitute for the described amphoacetate or amphopropionate compound is sodium cocoamphohydroxypropyl sulfonate. Sodium cocoamphoaetate is a preferred material.

The minimum proportion of the amphoteric detergent generally will be about 2.5% by weight of the final composition.

In the final shampoo composition, the mixture of anionic detergent and amphoteric surfactant will be in the range of about 4.5% to about 39% by weight, with the weight ratio of anionic detergent to amphoteric surfactant being in the range of about 10:1 to 0.8:1. In preferred shampoos, the mixture of anionic detergent and amphoteric surfactant will be in the range of about 7% to about 24% by weight, with a weight ratio of anionic detergent to amphoteric surfactant in the range of about 3:1 to 0.9:1. The most preferred compositions will contain about 10% to about 18% by weight of the mixture of anionic detergent and amphoteric surfactant.

Conditioning Agents

The essential conditioning agent which is employed in the inventive compositions is soluble in the above-described aqueous detersive surfactant mixture and generally will be selected from the group consisting of (1) essentially equimolar complexes of $C_8$–$C_{18}$ alkyl ethoxy carboxylic acids and $C_8$–$C_{18}$ alkyl ethoxy dimethyl amines; (2) a polyquaternary compound selected from the group consisting of a quaternized cellulosic polymer and a mixture of said quaternized cellulosic polymer with a non-cellulosic quaternary conditioning polymer; and (3) mixtures of the foregoing.

The equimolar complexes of $C_8$–$C_{18}$ alkyl ethoxy carboxylic acids and $C_8$–$C_{18}$ alkyl ethoxy dimethyl amines are believed to form water-insoluble amine salts which provide conditioning properties in the described compositions. Usually, the ethoxylated carboxylic acid will contain from 1 to 10 ethoxy groups and preferably from 2 to 6 ethoxy groups. On the other hand, the higher alkyl dimethyl amine may contain from 0 to 10 ethoxy groups. While the amine salts are believed to form when equimolar amounts of said carboxylic acid and said dimethyl amine are present, the presence of excess dimethylamine on a molar basis does not have an adverse effect on the conditioning properties of the amine salt and a slight molar excess of said amine may be preferred. Preferred carboxylic acids are the $C_{10}$–$C_{14}$ $(EtO)_{2-6}$ carboxylic acids and preferred amines are the $C_{14}$–$C_{18}$ alkyl and $C_{14}$–$C_{18}$ alkyl amido propyl dimethyl amines.

Generally the proportion of the amine salt formed by the complex of $C_8$–$C_{18}$ alkyl ethoxy carboxylic acid and the $C_8$–$C_{18}$ alkyl dimethyl amine will be about 0.05% to 5%, preferably 0.1% to 2.5%, and most preferably about 0.15% to 1.5%, by weight of the resultant composition. When this complex is used as sole conditioner, a low level of conditioning is perceived by the user. As stated herein, the water-insoluble conditioning complex of carboxylic acid and amine is soluble in the described aqueous shampoo, but is rendered water-insoluble when the resultant shampoo composition is diluted with water during use.

The suitable hair conditioning, cationic polymers are derivatives of natural polymers such as cellulose and gums. These derivatives generally are water-soluble to the extent of at least 0.5% by weight at 20° C. Generally, such polymers have more than 10 monomer units in their molecules and a molecular weight of about 1000 to about 1,000,000, preferably 2000 to 500,000. Usually, the lower the molecular weight, the higher the degree of substitution by the cationic, usually quaternary, group.

Suitable natural polymers which may be converted into the desired cationic polymers are hydroxy alkyl celluloses and alkyl hydroxy alkyl celluloses. Cationic hydroxy alkyl celluloses and their preparation are described in B.P. No. 1,166,062 assigned to Union Carbide. These hydroxy ethyl celluloses are marketed under the trade designation JR 125, JR 30M and JR 400 and are believed to have a molecular weight of 150,00 to 400,000 and a degree of substitution of a quaternary group of about 0.3. Alkyl hydroxy alkyl celluloses having the same formula as hydroxy alkyl cellulose, but with additional alkyl substituents at other sites on the anhydroglucose unit also are available. More particularly, the ethyl hydroxy ethyl celluloses are available under the tradename "Modocoll" with a molecular weight in the range of about 50,000 to 500,000 and a degree of substitution of about 0.1 to 0.8.

Other suitable natural cationic polymers are the galactomannan gums, e.g., guar gum and hydroxy alkylated guar gum. The molecular weight of guar gum is believed to be from about 100,000 to 1,000,000. A suitable cationic guar gum carrying the group —$CH_2CH=CH\ CH_2N\ (CH_3)_3Cl^-$ with a degree of substitution of about 0.2 to 0.8 is commercially available under the tradenames Jaguar C-17 and C-13. The preferred cationic cellulose polymer is Polyquaternium 10 which is a polymeric quaternary ammonium salt of hydroxyethyl cellulose reacted with a trimethyl ammonium substituted epoxide.

The proportion of the cationic natural polymer usually will be from about 0.05% to about 1%, preferably 0.1% to 0.8%, most preferably from 0.2% to 0.7%, by weight of the final composition. The cationic polymer provides for enhanced style control and conditioning. When Polyquaternium 10 is employed as the sole conditioning agent, a product with moderate conditioning results which is clear.

When the cationic natural cellulose or galactomannan gum polymers are present in the inventive compositions, up to about one half the weight of said natural polymer may be substituted by a second non-cellulosic, cationic polymer, having conditioning properties provided that the non-cellulosic cationic polymer is substantially soluble in the final composition. Exemplary of such cationic polymers are dialkyldiallyl ammonium salt (e.g., halide) homopolymers or copolymers, e.g., dimethyldiallyl ammonium chloride homopolymer, dimethyldiallyl ammonium chloride/ acrylamide copolymer containing at least 60% dimethyldiallyl ammonium chloride monomer, dimethyldiallyl ammonium chloride/acrylic acid copolymer containing at least 90% dimethyldiallyl ammonium chloride monomer, vinyl imidazole/vinyl pyrrolidone copolymers containing at least 50% vinyl imidazole and polyethyleneimine. Currently, the preferred cationic polymers are Merquat 100 [a polymer of diallyldimethyl ammonium chloride (charge density of 126)], Merquat 550 [a copolymer dimethyldiallyl ammonium chloride and acrylamide] and Luviquat 905 [a 95% vinyl imidazole/5% vinylpyrrolidone copolymer (charge density of 116)]. Other suitable non-cellulosic cationic polymers are disclosed in the CTFA Cosmetic Ingredient Dictionary under the designation "Polyquaternium" followed by a whole number. Often when a non cellulosic cationic polymer is present, the resultant shampoo composition will not be clear because the non-cellulosic polymer is not completely soluble in the shampoo.

Preferably, the mixture of the described water-insoluble equimolar complex of carboxylic acid and amine and the water soluble quaternized cellulose will be employed where high conditioning is desired.

The proportion of conditioning agent in the final shampoo composition generally will be from about 0.05% to 6%, preferably 0.1% to 3.3% and most preferably 0.3% to 1.5% by weight of the final shampoo composition.

Antistatic Agent

For static control, the inventive compositions will include a mixture of (1) a quaternary ammonium salt having the formula $R_9$, $R_{10}$, $R_{11}$, $R_{12}$ $N^+X^-$ wherein $R_9$ is a $C_{14}$–$C_{18}$ alkyl, $R_{10}$ and $R_{11}$ are each a $C_1$–$C_4$ alkyl, $R_{12}$ is $C_1$–$C_4$ alkyl or benzyl and $X^-$ is a salt forming cation selected from the group consisting of chloride, bromide, methosulfate and ethosulfate; and (2) a di-quaternary ammonium salt having the formula $(R_{13})_2R_{14}R_{15}N^+X^-$ wherein $R_{13}$ is a $C_{14}$–$C_{18}$ alkyl or alkylene group and $R_{14}$ and $R_{15}$ are each a $C_1$–$C_4$ alkyl group or a $(CH_2CH_2O)_nH$ group with at least one of $R_{14}$ and $R_{15}$ being a $(CH_2CH_2O)_nH$ group, n is an integer from 2 to 20 and X is a cation as set forth in (1) above; the weight ratio of the monoalkyl quaternary salt to dialkyl quaternary salt being from about 1:4 to 4:1, preferably 1:2 to 2:1.

Preferably, the lower alkyl groups in the foregoing compounds will contain one to two carbons, and the water-solubilizing group will be chlorine or bromine in the monoalkyl quaternary salt. Suitable monoalkyl quaternary compounds include cetyl trimethyl ammonium chloride and stearyl trimethyl ammonium chloride. Suitable di ($C_{14}$–$C_{18}$) alkyl ethoxylated quaternary compounds include di-stearyl $(EtO)_5$ ethyl ammonium ethosulfate and di-stearyl $(EtO)_{15}$ ethyl ammonium ethosulfate. The foregoing mixture of quaternary salts provides better antistatic properties than can be obtained using equivalent amounts of either quaternary salt alone. Such enhanced antistatic properties are unexpected and indicate coaction between the two salts. Further, the resultant mixture is soluble in the shampoo composition, thereby permitting manufacture of clear conditioning shampoos.

Generally the proportion of the static control mixture will be about 0.1% to 1%, preferably, 0.2% to 0.8% and most preferably 0.3% to 0.6%, by weight with the weight ratio of monoalkyl quaternary salt to dialkyl ethoxylated quaternary salt being in the range of 1:4 to 4:1, preferably 1:2 to 2:1. Usually, the antistatic properties increase as the proportion of the static control mixture increases.

The final essential component in the inventive compositions is water which provides an aqueous medium that constitutes the balance of the shampoo composition. Generally, the proportion of water will range from about 53% to about 95%, preferably, 68% to about 92%, and most preferably about 80% to about 87%, by weight of the resultant shampoos.

Optionally, the inventive shampoo compositions may include a non conditioning proportion of a water-insoluble silicone which is soluble in the surfactant mixture of the inventive shampoo as a hair plasticizing or hair smoothing agent. Suitable water-insoluble silicones are selected from the group consisting of polydimethyl siloxanes, polymethylphenyl siloxanes, polydimethyl siloxane-polyether copolymers wherein the ether group is polyoxyethylene and/or polyoxypropylene and mixtures thereof. Satisfactory silicones include polydimethyl siloxanes having a viscosity in the range of 100 cst to 500 cst (centistrokes) at 25° C. and polydimethyl siloxane-polyether copolymers having a viscosity of from 100 to 3000 cst @25° C. Said copolymers bear the CTFA designation dimethicone copolyol and satisfactory dimethicone copolyols are sold under the tradenames Dow Corning ® Q2-5220 and Dow Corning ® Q2-5324. Preferably, a mixture of a dimethicone copolyols—Q2-5220 and Q2-5324—will be employed in the shampoo composition.

When included, the proportion of water-insoluble silicone which is soluble in the detersive surfactant will be in the range of about 0.05% to about 0.30%, preferably from about 0.15% to 0.25%. The described proportion of silicone is a non-hair conditioning amount.

Typically, the inventive shampoo compositions will have a pH in the range of about 5.5 to 7.0, preferably 6.0 to 6.5. Also, the viscosity of said shampoos will be in the range of about 2500 cps to about 6500 cps, preferably 3500 cps to 5500 cps, as measured with a Brookfield RVT viscometer using a #4 spindle rotating at 20 rpm. Such viscosity has been found to be preferred by a significant segment of the ultimate consumers.

An important characteristic of the inventive shampoos which are ultra-mild to the skin is that the sum of the moles of anionic detergent and the moles of anionic hydrotrope is substantially equal to the sum of the moles of amphoteric detergent and the moles of cationic conditioning compound and the moles of quaternary anti static compounds. On a molar basis the ratio of anionic compounds to amphoteric compounds plus cationic compounds will be the range of about 0.8:1 to about 1.25:1, preferably about 0.9:1 to about 1.10:1, most preferably about 0.95:1 to about 1.05:1. It appears that the proportions of all of the essential ingredients are interrelated and must be controlled in order to achieve compositions having the desired mildness as well as desired foaming, cleaning, conditioning, clarity and viscosity characteristics.

These inventive shampoos are essentially unbuilt liquids, i.e., do not contain detergent building proportions of water-soluble inorganic or organic builder ingredients. Such shampoos can contain any of the usual adjuvants found in shampoo compositions provided that they do not interfere with the mildness, performance or aesthetic characteristics desired in the final products. Such additional ingredients include minor proportions of perfumes and coloring ingredients for aesthetic purposes; opacifiers such as ethylene glycol distearate or polystyrene; sequestering agents such as citrate or ethylenediamine tetreaacetate; preservatives such as formaldehyde or Kathon CG® or monomethyloldimethyl hydantoin; fluorescent agents; acids or bases for adjusting pH; and inert salts such as sodium sulfate. The total concentration of added ingredients usually will be less than 5%, preferably less than 3%, by weight of the total composition.

The inventive shampoos are prepared by admixing the cationic polymer, if any, with water at a temperature in the range of about 20° C. to 60° C., using sufficient agitation until a clear, homogeneous mixture is formed. Thereafter, the anionic surfactants, namely, the anionic detergent compound and the anionic hydrotropic agent are added while continuing the agitation until a homogeneous mixture is formed. Thereafter, the amphoteric detergent is added with agitation to the aqueous mixture of cationic polymer and anionic surfactants and agitation is continued until the resultant mixture is homogeneous. Next the disodium phosphate is added to adjust the pH to 6.0 –6.5. Then, if the carboxylic acid amine salt is present, a premix of the carboxylic acid and the desired amine is prepared with agitation at a temperature in the range 20° C. to 60° C. Optionally, perfume, polyethylene glycol oleate and di-$C_{14}$-$C_{18}$ alkyl ethoxylated quaternary ammonium salt are included in this premix which is mixed until homogeneity is achieved. Thereafter, the premix is added to the aqueous detergent mixture with agitation which continues until homogeneity is achieved. In the absence of the carboxylic acid amine salt, the ingredients optionally included in the premix are added directly to the detergent mixture. Finally the formula amounts of monoalkyl quaternary salt anti-stat preservative, if any, opacifier, if any, and color, if any, are added sequentially with agitation. During the manufacturing process, mixing is controlled to avoid foaming. The resultant composition is clear and has a pH in the range of about 5.5 to 7.0, preferably from about 6.0 to 6.5.

In the preferred process, the composition is prepared without the addition of external heat. Thus, the process temperature is controlled in the range of 20° C. to 30° C. Using this so-called "cold process" saves energy and the time required to raise or lower the temperature.

Normally, the viscosity and pH of the resultant product is checked before the product is filled into containers for sale. If necessary, additional anionic hydrotrope is added to decrease viscosity or polyethylene glycol (PEG) 18-propylene glycol oleate is added to increase viscosity. Also, if necessary, disodium phosphate dibasic or citric acid or other acid or base is added to adjust the pH. Preferably, the resultant composition is passed through a 20 mesh or equivalent filter prior to filling same into containers for sale.

The foaming properties of the inventive compositions are determined by diluting 15 cc of the resultant composition with 85 cc of 250 ppm water (40% $Mg^{++}$, 60% $Ca^{++}$), adding 3.0 grams of sebum soil and adjusting the temperature to 25° C. with agitation. Thereafter, the solution is added to a 500 ml graduated cylinder containing a plastic tube filled with water which has a volume of 25 cc. The 500 ml glass stoppered cylinder is then rotated through 40 half circles at a speed of 30 rpm. After removing the stopper, the foam volume is read. The cylinder then is removed from the rotation apparatus and placed on a table top. The time interval in seconds is recorded from the completion of rotation until the liquid level in the cylinder reaches 100 ml (75% of the liquid has drained) and the results are recorded as ml of foam/drainage time in seconds. Ml of foam and drainage times are then expressed on a scale of 1 to 10—1 poorest, 10 best—.

The conditioning properties are determined by combing hair tresses treated with the product using the fine teeth of the comb when wet and after drying. In this evaluation 3.2 gm tresses of virgin, European brown hair obtained from DeMeo Brothers, Inc. are prepared with the root end of the hair at the top of the tress. The tresses are rinsed with running tap water at 105° F. (40.5° C.) and then 1 cc of the test product is worked into the tress with the fingers for one minute. The treated tress is rinsed for 30 seconds and a second application of test product is worked into the tress for one minute followed by a 30 second rinsing. Then each tress is rinsed for 60 seconds with 105° F. running tap water and detangled by combing with the wide teeth of the comb. The wetted tresses are maintained wet with deionized water and are combed by expert judges using the fine teeth of the comb. The judges assign a rating of 1 to 10 for each tress, with 10 being easiest to comb. Each tress is combed by a minimum of 10 judges and the ratings are averaged. In the described procedure, the hair tresses are evaluated while wet. The procedure for dry combing is identical except that the hair tresses are dried before being combed.

In the test for evaluation of static, the hair tresses are treated with product as described above and dried. The dried tress is then combed by a skilled evaluator in a forceful, downward manner 20 times using the fine teeth of the comb. The static on each is then evaluated on a scale of 1 to 10 with 10 being excellent. Again, each tress is combed by 10 judges and the ratings are averaged. This evaluation is carried out in a constant temperature—constant humidity room.

Specific inventive liquid compositions are illustrated in the following examples. All quantities indicated in the examples or elsewhere in the specification are by weight unless otherwise indicated. A particularly preferred conditioning shampoo composition according to the described invention is set forth in example 1 below:

Example 1

| | % by wt. |
|---|---|
| Polyquaternium 10 | 0.35 |
| Polyquaternium 7**** | 0.24 |
| Sodium lauryl diethenoxy ether sulfate | 9.25 |
| Cocoamidopropyl dimethyl betaine | 5.1 |
| Sodium cumene sulfonate | 1.3 |
| Disodium hydrogen phosphate | 0.1 |
| Dimethicone copolyol (1500 cst) (a) | 0.1 |
| Dimethicone copolyol (400 cst) (b) | 0.1 |
| Laureth-3-carboxylic acid | 0.1 |
| Isostearymidopropyl dimethyl amine | 0.14 |
| PEG 55-propylene glycol oleate | ±.40 |
| PEG(4) di-stearylethonium ethosulfate | 0.2 |
| Cetrimonium chloride | 0.25 |
| Mixture of glycol distearate and steareth-4 and water** | 2.0 |
| Perfume | 0.8 |
| Kathon CG ® preservative | 0.07 |
| Water | q.s. |
| | 100.00 |

(a) Polymer of dimethylsiloxane with polyoxylethylene and/or polyoxypropylene side chains sold under the tradename Dow Corning ® Q2-5220
(b) Polymer of dimethylsiloxane with polyethylene oxide sold under the tradename Dow Corning ® Q2-5324
**Opacifying agent
****Non cellulosic copolymer of dimethyldiallyl ammonium chloride and acrylamide available under tradename Merquat 550

The foregoing shampoo composition is prepared by the preferred cold process at 20° C.–30° C. without addition of heat. In the cold process, the formula weight of Polyquaternium 10 is admixed with the formula amount of water with agitation to form a clear homogeneous mixture. Thereafter, the alkyl ether sulfate, the sodium cumene sulfonate, the betaine and the two siloxane ingredients are added to the aqueous polyquat solution in sequence with agitation. Mixing is continued after the addition of each ingredient until the resultant mixture is clear and homogeneous, with said agitation being controlled to avoid foaming. Next the disodium phosphate basic is added to said aqueous mixture. Then a homogeneous premix of the formula amounts of laureth-3-carboxylic acid, the isostearylamido-propyl dimethyl amine, the PEG 55-propylene glycol oleate, the PEG 4 distearyl ethonium ethosulfate and perfume is prepared with agitation at a temperature of 20° C.–30° C. and this premix is added to the aqueous detergent mixture with agitation which is continued until the resultant aqueous mixture is clear and homogeneous. Finally, the formula amounts of cetrimonium chloride, preservative and opacifier mixture are added in sequence to the foregoing mixture with agitation to form the opaque, homogeneous shampoo composition. The resultant shampoo composition is opaque, and has a viscosity of 4500 cps as measured with a Brookfield Viscometer using an RVT spindle #4 rotating at 20 rpm at 25° C. and has a pH of 6.25.

When the shampoo composition is tested using the above-described foaming, conditioning and static tests, the following results are obtained:

Foaming—9.0

Conditioning—9.0

Static—9.0

This composition provides very good conditioning effects when used to wash hair characterized as damaged because of prior treatment with bleaches, coloring agents or hair straighteners.

When the 9.25% of anionic alkyl diethenoxy ether sulfate is replaced by 7.4% by weight of sodium tetradecyl alkane sulfonates or 7.7% by weight of sodium $C_{14}$–$C_{16}$ alkene sulfonate or 7% by weight of ammonium lauryl sulfate—each being equimolar to said ether sulfate—, the resultant compositions have similar characteristics. The ratio of the sum of the moles of anionic detergent and benzene sulfonate to the sum of the moles of betaine, cationic conditioner and cationic anti-stat is 1.85:1.

Examples 2–4

The composition of Example 1 is repeated with the exceptions that the opacifying mixture is omitted and the concentration of Polyquaternium 10 is reduced from 0.35% by weight to 0.25%, 0.15% and 0.05% by weight respectively, with any balance being water. The resultant homogeneous shampoo compositions yield the foaming, conditioning, static and viscosity results set forth in Table A below:

TABLE A

| | Example | | |
|---|---|---|---|
| | 2 | 3 | 4 |
| Foaming | 9 | 8.5 | 8.0 |
| Conditioning | 8 | 6 | 4 |
| Static | 9 | 9 | 9 |
| Viscosity (cps) | 3800 | 3500 | 3200 |

The compositions of Examples 2–4 are stable, hazy liquids and show that the degree of conditioning in the inventive compositions can be varied from high to low by controlling the proportion of Polyquaternium 10—the cationic cellulose polymer.

Examples 5–8

The composition of Example 1 is repeated with the exception that the PEG 4 distearylethonium ethosulfate anti-static ingredient is omitted, the concentration of Polyquaternium 10 is reduced to 0.25% by weight and varying concentrations of centrimonium chloride are employed as the sole anti-static ingredient.

| | % by wt. | | | |
|---|---|---|---|---|
| | Ex 5 | Ex 6 | Ex 7 | Ex 8 |
| Polyquaternium 10 | 0.25 | 0.25 | 0.24 | 0.24 |
| Polyquaternium 7 | 0.24 | 0.24 | 0.24 | 0.24 |
| Sodium lauryl diethenoxy ether sulfate | 9.25 | 9.25 | 9.25 | 9.25 |

-continued

|  | % by wt. | | | |
|---|---|---|---|---|
|  | Ex 5 | Ex 6 | Ex 7 | Ex 8 |
| Cocoamidopropyl dimethyl betaine | 5.1 | 5.1 | 5.1 | 5.1 |
| Sodium cumene sulfonate | 1.3 | 1.3 | 1.3 | 1.3 |
| Disodium hydrogen phosphate | 0.1 | 0.1 | 0.1 | 0.1 |
| Dimethicone copolyol (1500 cst) | 0.1 | 0.1 | 0.1 | 0.1 |
| Dimethicone copolyol (400 cst) | 0.1 | 0.1 | 0.1 | 0.1 |
| Laureth-3-carboxylic acid | 0.1 | 0.1 | 0.1 | 0.1 |
| Isostearymidopropyl dimethyl amine | 0.14 | 0.14 | 0.14 | 0.14 |
| PEG 55 propylene glycol oleate | 0.4 | 0.4 | 0.4 | 0.4 |
| PEG(4) di-stearylethonium ethosulfate | — | — | — | — |
| Cetrimonium chloride | 0.0625 | .125 | .25 | 0.50 |
| Opacifier mixture*** | 2.0 | 2.0 | 2.0 | 2.0 |
| Water, perfume, preservative | q.s | q.s | q.s | q.s |
|  | 100.0 | 100.0 | 100.0 | 100.00 |

***The opacifying agent of Example 1

The foregoing compositions are prepared in the same manner as Example 1 and all are stable, opaque liquids whose foaming, conditioning and anti-static properties and viscosity are set forth in Table B below:

TABLE B

|  | Example | | | |
|---|---|---|---|---|
|  | 5 | 6 | 7 | 8 |
| Foaming | 8.50 | 8.5 | 8.0 | 7.0 |
| Conditioning | 6.75 | 6.75 | 7.0 | 7.0 |
| Static | 4.5 | 5.5 | 7.0 | 7.0 |
| Viscosity (cps 24° C.) | 2700 | 2900 | 4300 | 2000 |

The foregoing tabulation shows that when the cetyltrimethyl ammonium chloride is the sole anti-stat employed, a maximum anti-static level of 7.0 is attained. Further, at the maximum concentration of 0.5%, the viscosity of the resultant composition is decreased to 2,000 cps which is outside the desired viscosity range. Additionally, Table B shows that varying the concentration of the mono-alkyl quaternary anti-stat ingredient varies the foaming and conditioning properties.

Examples 9–12

Examples 9–12 describe the compositions of Examples 5–8 with the exception that the centrimonium chloride anti-stat ingredient is omitted and varying concentrations of the ethoxylated distearyl ethonium ether sulfate are included as the sole anti-static ingredient.

|  | % by wt. | | | |
|---|---|---|---|---|
|  | Ex 9 | Ex 10 | Ex 11 | Ex 12 |
| Polyquaternium 10 | 0.24 | 0.25 | 0.25 | 0.25 |
| Polyquaternium 7 | 0.24 | 0.24 | 0.24 | 0.24 |
| Sodium lauryl diethenoxy ether sulfate | 9.25 | 9.25 | 9.25 | 9.25 |
| Cocoamidopropyl dimethyl betaine | 5.1 | 5.1 | 5.1 | 5.1 |
| Sodium cumene sulfonate | 1.3 | 1.3 | 1.3 | 1.3 |
| Disodium hydrogen phosphate | 0.1 | 0.1 | 0.1 | 0.1 |
| Dimethicone copolyol (1500 cst) | 0.1 | 0.1 | 0.1 | 0.1 |
| Dimethicone copolyol (400 cst) | 0.1 | 0.1 | 0.1 | 0.1 |
| Laureth-3-carboxylic acid | 0.1 | 0.1 | 0.1 | 0.1 |
| Isostearymidopropyl dimethyl amine | 0.14 | 0.14 | 0.14 | 0.14 |
| PEG 55 propylene glycol oleate | 0.4 | 0.4 | 0.4 | 0.4 |
| PEG(4) di-stearylethonium ethosulfate | 0.1 | 0.2 | 0.3 | 0.5 |
| Cetrimonium chloride | — | — | — | — |
| Opacifier mixture*** | 2.0 | 2.0 | 2.0 | 2.0 |
| Water, perfume, preservative | q.s | q.s | q.s | q.s |
|  | 100.0 | 100.0 | 100.0 | 100.00 |

***The opacifying agent of Example 1

The resultant compositions are prepared by the same process employed in Example 1 and are stable opaque liquids having the characteristics described in Table C.

TABLE C

|  | Example | | | |
|---|---|---|---|---|
|  | 9 | 10 | 11 | 12 |
| Foaming | 8.5 | 8.5 | 8.75 | 8.75 |
| Conditioning | 7.5 | 8.0 | 8.0 | 8.5 |
| Static | 4.0 | 5.0 | 5.5 | 6.5 |
| Viscosity (cps 24° C.) | 3700 | 3800 | 3900 | 4200 |

Table C indicates that the maximum anti-static level attained using the described distearyl ethosulfate as the sole anti-static agent is 6.5. Again, the tabulation shows that varying the concentration of the anti-static agent varies the foaming and conditioning properties as well as the viscosity of the resultant conditioning shampoos.

Example 13

When the composition of Example 9 is repeated with the exception that the PEG(4) distearylethonium ethosulfate is omitted and replaced by the same amount of water, the resultant shampoo is a stable opaque liquid having a viscosity of 3500 cps at 24° C. and a pH of 6.2. When evaluated using the same tests employed in Example 1, its static value is 3.0 and the foaming and conditioning values are 8.5 and 6.5 respectively.

The foregoing examples point out that optimum anti-static properties in the inventive compositions are attained when the mono-$C_{14}$–$C_{18}$ alkyl quaternary salt and the ethoxylated di-quaternary ammonium salt are used in combination. More specifically, the composition of Example 1 containing 0.2% by weight of ethoxylated di-stearyl quat and 0.25% of the cetyl quat has an anti-static value of 9; whereas, the composition of Example 12 containing 0.5% by weight of ethoxylated distearyl quat has an anti-static value of 6.5 and the composition of Example 8 containing 0.5% by weight of cetyl trimethyl ammonium chloride has an anti-static value of 7.0. These results indicate coaction between the individual anti-stat ingredients which is quite surprising.

Examples 14–15

The following examples describe inventive compositions wherein the conditioning agent is a mixture of Polyquaternium 10 and the described carboxylic acid-amine complex.

|  | % by wt. | |
| --- | --- | --- |
|  | Ex 14 | Ex 15 |
| Polyquaternium 10 | 0.5 | 0.4 |
| Sodium lauryl diethenoxy ether sulfate | 9.25 | 9.25 |
| Cocoamidopropyl dimethyl betaine | 5.1 | 5.1 |
| Sodium cumene sulfonate | 1.3 | 1.3 |
| Disodium hydrogen phosphate | 0.1 | 0.1 |
| Dimethicone copolyol (1500 cst) | 0.1 | 0.1 |
| Dimethicone copolyol (400 cst) | 0.1 | 0.1 |
| Laureth-3-carboxylic acid | 0.1 | 0.1 |
| Isostearymidopropyl dimethyl amine | 0.14 | 0.14 |
| PEG 55 propylene glycol oleate | 0.4 | 0.4 |
| PEG(4) di-stearylethonium ethosulfate | 0.2 | 0.2 |
| Cetrimonium chloride | 0.25 | 0.25 |
| Water, perfume, preservative | q.s | q.s |
|  | 100.0 | 100.0 |

The resultant shampoo compositions are clear liquids whose foaming conditioning and anti-static values are set forth below together with the viscosity of the composition.

|  | Example | |
| --- | --- | --- |
|  | 14 | 15 |
| Foaming | 9.0 | 8.5 |
| Conditioning | 9.5 | 8.5 |
| Anti-Static | 8.5 | 9.0 |
| Viscosity (cps 24° C.) | 4500 | 4200 |

Example 16

A highly preferred, ultra-mild conditioning shampoo composition follows:

|  | % by wt. |
| --- | --- |
| Polyquaternium 10 | 0.60 |
| Sodium lauryl diethenoxy ether sulfate | 7.0 |
| Cocoamidopropyl dimethyl betaine | 7.8 |
| Sodium cumene sulfonate | 1.3 |
| Disodium hydrogen phosphate | 0.3 |
| Dimethicone copolyol (1500 cst) | 0.1 |
| Dimethicone copolyol (400 cst) | 0.1 |
| Laureth-3-carboxylic acid | 0.1 |
| Isostearymidopropyl dimethyl amine | 0.14 |
| PEG 55 propylene glycol oleate | ±.40 |
| PEG(4) di-stearylethoniuim ethosulfate | 0.2 |
| Cetrimonium chloride | .25 |
| Mixture of glycol distearate, steareth 4 and water | 2.0 |
| Perfume | 0.5 |
| Kathon CG ® preservative | 0.07 |
| Yellow color solution | 0.14 |
| Water | q.s. |
|  | 100.0 |

The foregoing shampoo composition is prepared in the manner described in Example 1 to form an opaque, liquid shampoo composition having a viscosity of 4500 cps, at 24° C. and a pH of 6.2. It has anti-static value of 9 and foaming and conditioning values of 7 and 7 respectively. This shampoo is very mild to the skin and the mole ratio of the sum of the moles of anionic detergent and benzene sulfonate to the sum of the moles of betaine, polyquat conditioner and cationic anti-stats is 1.0:1.0.

Although the relationship between mildness and the need for substantially balanced molar proportions of anionic materials—detergent plus hydrotropic sulfonate/sulfate— and amphoteric plus cationic ingredients is not understood, it is believed that the anionic ingredients and the amphoteric plus cationic materials form a complex—possibly two complexes. The existence of at least one complex is suggested by the improved mildness and the increased viscosity of the resultant mixtures. It is further suggested by the improved conditioning properties when conditioning agents are included. While the actual mechanism is not understood, the efficacy of the resultant compositions is apparent at use concentrations thereof.

Examples 17 and 18

These examples show other compositions which are within the scope of the described invention.

|  | % by wt. | |
| --- | --- | --- |
| Polyquaternium 10 | 0.6 | 0.3 |
| Sodium lauryl diethenoxy ether sulfate | 10.5 | 3.5 |
| Cocoamidopropyl dimethyl betaine | 7.8 | 3.9 |
| Sodium cumene sulfonate | 1.95 | 0.65 |
| Disodium hydrogen phosphate | 0.45 | 0.15 |
| Laureth-3-carboxylic acid | 0.15 | 0.05 |
| Isostearymidopropyl dimethyl amine | 0.21 | 0.07 |
| Dimethicone copolyol (1500 cst) | 0.1 | 0.1 |
| Dimethicone copolyol (400 cst) | 0.1 | 0.1 |
| PEG 55 propylene glycol oleate | 0.6 | 0.2 |
| PEG(4) di-stearylethonium ethosulfate | 0.2 | 0.2 |
| Cetyltrimethyl ammonium chloride | 0.20 | 0.125 |
| Water | q.s | q.s |
|  | 100.0 | 100.0 |

The anti-static properties of the resultant shampoo compositions are very good.

The clear and opaque compositions of the present invention can also be formulated as anti-dandruff shampoos, by employing therein about 0.10% to about 4% by weight of a conventional anti-dandruff therapeutic agent which is soluble in the detersive surfactant mixture. Such agents include: 1-imidazolyl-1-(4-chlorophenoxy)-3,3-dimethylbutan-2-one (Climbazole); acetylsalicylic acid; salicylic acid; 2,4,4,'-trichloro-2'-hydroxy diphenyl ether (triclosan); 1-acetyl-4-(4-((2-(2,4-dichlorophenyl)-2-(1H-imidazolyl-1-methyl)-1,3-dioxolan-4-yl)methoxy)phenyl)-piperazine (ketoconazole); 1-hydroxy-4-methyl6-(2,4,4-trimethylpentyl)-2-pyridone monoethonolamine salt (piroctone olamine); and mixtures thereof. Climbazole is the preferred anti-dandruff therapeutic agent.

Examples 19 and 20

These examples illustrate clear, ultra-mild, antidandruff compositions which are within the scope of the described invention.

|  | % by wt. | |
| --- | --- | --- |
|  | 19 | 20 |
| Polyquaternium 10 | 0.6 | 0.6 |
| Sodium lauryl diethenoxy ether sulfate | 7.0 | 7.0 |
| Cocoamidopropyl dimethyl betaine | 7.8 | 7.8 |
| Sodium cumene sulfonate | 1.3 | 2.17 |
| Disodium hydrogen phosphate | 0.1 | 0.3 |
| Laureth-3 carboxylic acid | 0.1 | 0.1 |
| Isostearymidopropyl dimethyl amine | 0.14 | 0.14 |
| Dimethicone copolyol (1500 cst) | 0.1 | — |
| Dimethicone copolyol (400 cst) | 0.1 | — |
| PEG 55-propylene glycol oleate | 0.36 | — |

|                                         | % by wt. | |
| --------------------------------------- | -------- | ------ |
|                                         | 19       | 20     |
| PEG(4) distearylethonium ethosulfate    | 0.2      | 0.2    |
| Cetyltrimethyl ammonium chloride        | 0.25     | 0.25   |
| Climbazole                              | 0.5      | 0.5    |
| Color, perfume, preservative, water     | q.s      | q.s.   |
|                                         | 100.00   | 100.00 |

The proportions of anionic materials and amphoteric plus cationic materials are substantially balanced in the foregoing compositions to provide ultra-mildness.

The invention has been described with respect to various examples and illustrations thereof but is not to be limited to these because it is clear that one of skill in the art, with the present description before him, will be able to utilize substitutes and equivalents without departing from the invention.

What is claimed is:

1. An effective conditioning shampoo composition which is free of conditioning amounts of silicone conditioning agents comprising by weight:
   A. about 5% to about 40% of a detersive surfactant mixture of:
      (1) an anionic detergent selected from the group consisting of $C_8$–$C_{18}$ alkyl sulfates, $C_8$–$C_{18}$ alkyl ethenoxy ether sulfates containing 1 to 12 ethenoxy groups in the molecule, $C_8$–$C_{18}$ acyl isethionates, $C_{10}$–$C_{20}$ alkyl sulfonates, $C_{10}$–$C_{22}$ alkene sulfonates, and mixtures thereof; and
      (2) an amphoteric surfactant selected from the group consisting of $C_8$–$C_{18}$ alkyl betaines, and sulfobetaines, $C_8$–$C_{18}$ alkyl amido, $C_2$–$C_3$ alkyl betaines and sulfobetaines, $C_8$–$C_{18}$ alkyl amphoacetates, $C_8$–$C_{18}$ alkyl amphopropionates, and mixtures thereof; the weight ratio of said anionic detergent to said amphoteric detergent being in the range of about 10:1 to 0.8:1;
   B. about 0.05% to about 6% of a conditioning agent is selected from the group consisting of:
      (1) 0.05% to 5% of a complex of essentially equimolar amounts of a $C_8$–$C_{18}$ $(EtO)_{1-10}$ carboxylic acid, and a $C_8$–$C_{18}$ alkyl $(EtO)_{0-10}$ dimethyl amine;
      (2) 0.05% to 1.0% of a polyquaternary compound selected from the group consisting of a quaternized cellulosic polymer and a mixture of said quaternized cellulosic polymer with a non-cellulosic quaternary conditioning polymer; and
      (3) mixtures of the foregoing;
   C. 0.1% to 1% of a static control mixture of:
      (1) a quaternary ammonium salt having the formula $R_9$, $R_{10}$, $R_{11}$, $R_{12}$ $N^+X^-$ wherein $R_9$ is a $C_{14}$–$C_{18}$ alkyl, $R_{10}$ and $R_{11}$ are each a $C_1$–$C_4$ alkyl, $R_{12}$ is $C_1$–$C_4$ alkyl or benzyl and $X^-$ is a salt forming cation selected from the group consisting of chloride, bromide, methosulfate and ethosulfate; and
      (2) a di-quaternary ammonium salt having the formula $(R_{13})_2R_{14}R_{15}N^+X^-$ wherein $R_{13}$ is a $C_{14}$–$C_{18}$ alkyl or alkylene group and $R_{14}$ and $R_{15}$ are each a $C_1$–$C_4$ alkyl group or a $(CH_2CH_2O)_nH$ group with at least one of $R_{14}$ and $R_{15}$ being a $(CH_2CH_2O)_nH$ group, n is an integer from 2 to 20 and X is a cation as set forth in C(1) above; the weight ratio of the monoalkyl quaternary salt to dialkyl quaternary salt being from about 1:4 to 4:1; and
   D. the balance being an aqueous medium; said compositions exhibiting enhanced antistatic properties as compared to the same compositions containing either said monoalkyl quaternary salt or said dialkyl quaternary salt as the sole antistatic ingredient.

2. A shampoo composition according to claim 1 wherein said conditioning agent includes a quaternized cellulosic polymer.

3. A shampoo composition according to claim 2 wherein said conditioning agent is a mixture of said cellulosic polymer and a non-cellulosic quaternary conditioning polymer.

4. A shampoo composition according to claim 3, wherein said mixture of conditioning agents includes, in addition, said complex of said carboxylic acid and said alkyl amine.

5. A shampoo composition according to claim 2 which includes in addition about 0.5 to 5% by weight of an anionic hydrotropic $C_1$–$C_3$ alkyl benzene sulfonate or $C_5$–$C_6$ alkyl sulfate.

6. A shampoo composition according to claim 5 wherein the mole ratio of the sum of the moles of anionic detergent and anionic benzene sulfonate to the sum of the moles of amphoteric detergent and the moles of cationic conditioning agent and antistatic agent is in the range of 0.9:1.0 to 1.1:1.0.

7. A shampoo composition according to claim 5 which includes, in addition, from 0.05% to 0.30% by weight of a water-insoluble silicone selected from the group consisting of polydimethyl siloxanes, polymethylphenyl siloxanes, polydimethylsiloxane-polyether copolymers and mixtures thereof.

8. An effective conditioning shampoo composition which is free of conditioning amounts of silicone conditioning agents comprising by weight:
   A. about 8% to about 28% of a detersive surfactant mixture of:
      (1) an anionic detergent selected from the group consisting of water soluble salts of $C_8$–$C_{18}$ alkyl sulfates and $C_8$–$C_{18}$ alkyl (ethenoxy )1–5 ether sulfates; and
      (2) an amphoteric surfactant selected from the group consisting of $C_8$–$C_{18}$ alkyl betaines and $C_8$–$C_{18}$ alkyl amido $C_2$–$C_3$ alkyl betaines;
   B. about 0.1% to 3.3% of a water-insoluble conditioning agent selected from the group consisting of:
      (1) 0.10% to about 2.5% of a complex of essentially equimolar amounts of a $C_8$–$C_{18}$ $(EtO)_{2-}$ carboxylic acid, and a $C_8$–$C_{18}$ alkyl $(EtO)_{0-}$ dimethyl amine;
      (2) about 0.1% to about 0.8% of a polyquaternary compound selected from the group consisting of a quaternized cellulosic polymer and a mixture of said quaternized cellulosic polymer with a non-cellulosic quaternary conditioning polymer; and
      (3) mixtures of the foregoing; and
   C. 0.2% to 0.8% of a static control mixture of:
      (1) a quaternary ammonium salt having the formula $R_9$, $R_{10}$, $R_{11}$, $R_{12}$ $N^+X^-$ wherein $R_9$ is a $C_{14}$–$C_{18}$ alkyl, $R_{10}$ and $R_{11}$ are each a $C_1$–$C_2$ alkyl, $R_{12}$ is $C_1$–$C_2$ alkyl $X^-$ is a salt forming cation selected from the group consisting of chloride, methosulfate and ethosulfate; and
      (2) a di-quaternary ammonium salt having the formula $(R_{13})_2R_{14}R_{15}N^+X^-$ wherein $R_{13}$ is a $C_{14}$–$C_{18}$ alkyl or alkylene group and $R_{14}$ and $R_{15}$ are each a $C_1$–$C_2$ alkyl group or a $(CH_2CH_2O)_nH$ group with at least one of $R_{14}$ and $R_{15}$ being a $(CH_2CH_2O)_nH$ group, n is an integer from 2 to 20 and X is a cation as set forth in C(1) above; the weight ratio of the monoalkyl quaternary salt to dialkyl quaternary salt being from about 1:2 to 2:1;
   D. about 68% to about 92% of water; said compositions exhibiting enhanced antistatic properties as compared to the same composition containing either said monoalkyl quaternary salt or said dialkyl quaternary salt as the sole antistatic ingredient.

9. A shampoo composition according to claim 8 wherein said conditioning agent includes a quaternized cellulosic polymer.

10. A shampoo composition according to claim 9 wherein said conditioning agent is a mixture of said cellulosic polymer and a non-cellulosic quaternary conditioning polymer.

11. A shampoo composition according to claim 10 which includes, in addition, 0.5% to 5% by weight of an anionic hydrotropic $C_1$–$C_3$ alkylbenzene sulfonate or a $C_5$–$C_6$ alkyl sulfate.

12. A shampoo composition according to claim 11 wherein said conditioning mixture includes, in addition, said complex of said carboxylic acid and said alkyl amine.

13. A shampoo composition according to claim 12 which includes, in addition, from 0.15% to 0.25% by weight of a mixture of polydimethyl siloxane-polyether copolymers.

14. A shampoo composition according to claim 13 wherein the mole ratio of the sum of the moles of anionic detergent and anionic benzene sulfonate to the sum of the moles of amphoteric detergent and the moles of cationic conditioning agent is in the range of 0.9:1.0 to 1.1:1.0.

* * * * *